United States Patent
Pause et al.

(10) Patent No.: US 11,207,330 B2
(45) Date of Patent: Dec. 28, 2021

(54) MIRTAZAPINE FOR USE IN MEDICATION OVERUSE HEADACHE BASED ON TENSION-TYPE HEADACHE

(71) Applicants: Curatis AG, Liestal (CH); Rigshospitalet—Glostrup, Glostrup (DK); The University of Copenhagen, Copenhagen K (DK)

(72) Inventors: Arnim Pause, Montreal (CA); Lars Bendtsen, Slagelse (DK); Rigmor Jensen, Herfoelge (DK); Jes Olesen, Hellerup (DK)

(73) Assignees: Curatis AG, Liestal (CH); Rigshospitalet—Glostrup, Glostrup (DK); The University of Copenhagen, Copenhagen K (DK)

( * ) Notice: Subject to any disclaimer, the term of this patent is extended or adjusted under 35 U.S.C. 154(b) by 0 days.

(21) Appl. No.: 16/948,813

(22) Filed: Oct. 1, 2020

(65) Prior Publication Data

US 2021/0015828 A1 Jan. 21, 2021

Related U.S. Application Data

(63) Continuation of application No. PCT/EP2020/063005, filed on May 11, 2020.

(30) Foreign Application Priority Data

May 12, 2019 (EP) ..................................... 19173972

(51) Int. Cl.
*A61K 31/55* (2006.01)
*A61P 25/06* (2006.01)

(52) U.S. Cl.
CPC .............. *A61K 31/55* (2013.01); *A61P 25/06* (2018.01)

(58) Field of Classification Search
CPC ................................ A61K 31/55; A61P 25/06
See application file for complete search history.

(56) References Cited

FOREIGN PATENT DOCUMENTS

| EP | 1 132 082 | 9/2001 |
| EP | 1 242 092 | 7/2003 |

OTHER PUBLICATIONS

Diener et al. "*Headache Associated with Chronic Use of Substances,*" The Secondary Headaches, Chapter 115, The Headaches, 2nd Edition, p. 871-877, edited by J. Olesen, P. Tfelt-Hansen, and K.M.A. Welch, Lippincott Williams & Wilkins, Philadelphia, 2000. International Search Report dated Jul. 22, 2020 in PCT/EP2020/063005.
Written Opinion dated Jul. 22, 2020 in PCT/EP2020/063005.
Extended European Search Report dated Oct. 18, 2019 in European Application No. 19173972.1.
Bendtsen et al., "*Combination of low-dose mirtazapine and ibuprofen for prophylaxis of chronic tension-type headache,*" European Journal of Neurology 2007, 14: 187-193.
Bendtsen et al., "*Mirtazapine is effective in the prophylactic treatment of chronic tension-type headache,*" Neurology 62, 2004, pp. 1706-1711.
Bendtsen et al., "*Reference programme: Diagnosis and treatment of headache disorders and facial pain. Danish Headache Society, 2nd Edition, 2012,*" J Headache Pain (2012) 13 (Suppl 1): S1-S29.
Bigal et al., "*Prevalence and characteristics of allodynia in headache sufferers,*" Neurology 2008; 70; 1525-1533.
Dodick et al., "*Central Sensitization Theory of Migraine: Clinical Implications,*" Headache 2006; 46[Suppl 4]:S182-S191.
Dong et al., "*Application of ICHD-II Criteria in a Headache Clinic of China,*" PLoS One, 2012, 7(12):e50898, 6 pages.
Fritsche et al., "*Drug-Induced Headache: Long-Term Follow-Up of Withdrawal Therapy and Persistence of Drug Missue,*" Eur. Neurol. 2001; 45: 229-235.
Kaji et al., "*Efficacy of Mirtazapine for treatment of medication-overuse headache (moh)—a in 3 cases of moh,*" International Headache Society, 2011, Cephalalgia 31 (Suppl. 1), p. 66.
Katsarava et al., "*Medication overuse headache: rates and predictors for relapse in a 4-year prospective study,*" Cephalalgia. 2004; 25:12-15.
Justine M. Kent, "*SNaRIs, NaSSAs, and NaRIs: new agents for the treatment of depression,*" Lancet 2000; 355: 911-918.
Mitsikostas et al., "*Treatment and outcome in medication overuse headache patients,*" The Journal of Headache and Pain 2013, 14(Suppl 1): P180.
Monteith et al., "*Tension-type Headache With Medication Overuse: Pathophysiology and Clinical Implications,*" Curr Pain Headache Rep. Dec. 2009; 13(6): 463-469.
Olesen et al., "*The International Classification of Headache Disorders, 3rd edition (beta version),*" Cephalalgia, International Headache Society, 2013, 33(9) 629-808.
Schnider et al., "*Long-term outcome of patients with headache and drug abuse after inpatient withdrawal: five-year follow-up,*" Cephalalgia 1996; 16:481-485.
Herman G. M. Westenberg, "*Pharmacology of Antidepressants: Selectivity or Multiplicity?,*" J. Clin. Psychiatry 1999; 60 [suppl. 17]: 4-8.
Zeeberg et al., "*Discontinuation of medication overuse in headache patients: recovery of therapeutic responsiveness,*" Cephalalgia, 2006, 26: 1192-1198.
Zhang et al., "*Mismatch negativity in chronic tention-type headache with and without medication-overuse,*" Neurology Asia 2013; 18(2): 183-189.
Hagen, et al. "Management of medication overuse headache: 1-year randomized multicentre open-label trial," *Cephalalgia*, 2008, 29, 221-232.

*Primary Examiner* — Sahar Javanmard
(74) *Attorney, Agent, or Firm* — Grüneberg and Myers PLLC

(57) ABSTRACT

Mirtazapine is useful for the treatment and/or prophylaxis of medication overuse headache based on tension-type headache. Moreover, a pharmaceutical composition and/or the use of mirtazapine for the manufacture of a medicament, are useful against medication overuse headache based on tension-type headache, and the treatment of medication overuse headache based on tension-type headache.

12 Claims, 2 Drawing Sheets

MIRTAZAPINE FOR USE IN MEDICATION OVERUSE HEADACHE BASED ON TENSION-TYPE HEADACHE

CROSS-REFERENCE TO RELATED APPLICATIONS

The present application is a continuation of PCT/EP2020/063005, filed on May 11, 2020, and claims the benefit to European patent application No. 19173972.1, filed on May 12, 2019, the content of each of which is hereby incorporated by reference in its entirety.

BACKGROUND OF THE INVENTION

Field of the Invention

The present invention relates to the field of headache treatment. In particular, it relates to mirtazapine for use in the treatment of medication overuse headache (MOH) based on tension-type headache (TTH). Moreover, the present invention concerns a pharmaceutical composition and/or the use of mirtazapine for the manufacture of a medicament, all against medication overuse headache based on tension-type headache, and a method of treatment of medication overuse headache based on tension-type headache.

Discussion of the Background

Headache is one of the most prevalent disorders in human society and is responsible for substantial socioeconomic expenses. Headaches cause substantial individual impact on work productivity and employer and societal burden from direct medical costs, lost work time, and underemployment, and, in more severe persistent headache, unemployment. The lost work time costs greatly exceed medical care costs. The term headache comprises numerous kinds of different types of headache, which differ from each other for instance in the character of pain, its location, frequency, and in particular in the different pathophysiology involved. Notably due to the different disease mechanisms, it is necessary to correctly diagnose the type of headache in a patient, then specifically choosing the appropriate medication.

The most common kind of primary headache is tension-type headache, whereby the lifetime prevalence in the general population in diverse studies is ranging between 30% and 78% (Cephalalgia 33(9) 629-808; DOI: 10.1177/0333102413485658). Tension-type headache can radiate from the lower back of the head, the neck, eyes or other muscle groups and typically affects both sides of the head and does not get worse during physical activity. Tension type headache has a very high socio-economic impact. Although this type of headache was previously considered to be primarily psychogenic, new studies strongly suggest a neurobiological basis, at least for the more severe and frequent subtypes of tension-type headache. Tension-type headache can be subdivided into infrequent episodic tension-type headache (ieTTH), frequent episodic tension-type headache (feTTH) and chronic tension-type headache (cTTH). Their specific pathophysiology will be discussed below.

An important factor in the long-term prognosis of TTH is the overuse of acute medications used to treat headache. Patients which tend to use acute medication too often to treat their headache, are predestined for medication overuse headache. Instead of curing the pain, overuse leads to even heavier secondary headache which is much more difficult to treat. Economically, medication overuse headache is the most costly kind of headache.

Chronic daily headache occurs in 4.1% of the general population, and chronic tension-type headache and medication overuse headache (MOH) occur in approximately 2.2% and 1.5%, respectively (Monteith et al, Curr Pain Headache Rep. 2009 December; 13(6):463-469).

According to a meta-analysis summarizing 29 studies comprising a total of 2612 patients with chronic drug-induced headache (Diener et al. Headache associated with chronic use of substances. In: Olesen, J.; Tfelt-Hansen, P.; Welch, K M A., editors. The Headaches. edn 2. Philadelphia: Lippincott Williams and Wilkins; 1999. p. 871-878), 65% reported migraine as their primary headache disorder, whereas 27% reported TTH and 8% reported mixed or other headaches as their primary headaches. To date, it is still unclear why MOH is more frequent in migraine than TTH. However, tension-type headache with medication overuse headache carries the worst prognosis.

Tension-type headache is an ill-defined heterogeneous syndrome, which is often diagnosed by the absence of migrainous features. Hyperexcitable peripheral nociceptors are a likely etiology of the peripheral mechanism of tension-type headache. Physical triggers may include muscle strain during intense mental activity or poor posture. Infrequent tension-type headache may be the result of peripheral mechanisms, whereas frequent tension-type headache or chronic tension-type headache may be peripheral and centrally mediated.

Central sensitization is a process in migraine whereby the stimulus required to generate a response decreases, while the amplitude of the response of any given stimulus increases (Dodick et al, Headache. 2006; 46(Suppl 4):182-S191). Repetitive activation of the trigeminal nerve may decrease in nociceptive thresholds and expand the receptive field through functional changes in the neurons of the trigeminal nucleus caudalis. Central sensitization is associated with hyperexcitability in the trigeminal nucleus caudalis. Cutaneous allodynia is the clinical correlate of central sensitization. In a population-based study, the prevalence and severity of cutaneous allodynia were the lowest in severe tension-type headache and other forms of chronic daily headache and the highest in transformed migraine (Bigal et al, Neurology. 2008; 70:1525-1533). The above findings suggest that tension-type headache and migraine differ substantially in respect of central sensitization.

A further difference in medication overuse based on tension-type headache and medication overuse headache based on migraine is the long-term relapse rate. In one study that followed 96 patients with medication overuse headache, the relapse rates at 1 and 4 years were 41% and 45%, respectively (Katsarava et al, Cephalalgia. 2005; 25:12-15). The study identified several important risk factors. The relapse rate depended on the type of analgesics being misused: 71% for analgesics, 27% for ergots, and 21% for triptans. The relapse rate also depended on the type of primary headache.

The relapse rate was lower for patients with migraine (32%) and higher for patients with a combination of migraine and tension-type headache (70%) and tension-type headache alone (91%). In another prospective study of 38 patients with a 5-year follow-up, the relapse rate was 40%, and tension-type headache was also a predictor of relapse (Schnider et al, Cephalalgia. 1996; 16:481-485).

Zeeberg et al. (Cephalalgia, 2006; 26: 1192-1198) reported that discontinuation of overused drug caused a reduction in chronic tension-type headache (CTTH) frequency by 18% whereas reduction in chronic migraine (CM) was 51%. A subgroup analysis revealed that relapse was dependent on only two main factors: the previous headache disorder and the specific overused drug. CTTH patients had a significantly higher relapse rate (77%) than CM patients (23%) while patients overusing combination analgesics (58%) showed significantly higher relapse rate than patients overusing triptans (22%) or ergotamines (19%; Fritsche et al, Eur. Neurol. 2001; 45, 229-235).

Zhang et al. (Neurology Asia. 2013; 2: 183-189) report that MOH behaves more like chronic tension type headache than chronic migraine in terms of frequency, intensity and duration. The mechanisms of the pre-existing headache such as CM or CTTH contributes to the pathogenesis of MOH. In CTTH peripheral mechanism play a role such as altered myofascial nociception and central mechanisms such as inadequate endogenous pain control. Activation of the trigeminovascular system and initiation of cortical spreading depression play a role in CM pathogenesis. The pathophysiology of MOH originating from CTTH was shown to be caused by the central sensitization and deficits of endogenous pain control.

Dong et al. report (PLoS One. 2012; 12:e50898. doi: 10.1371) that in a study with almost 2000 patients the incidence of different types of chronic daily headache (CDH) was measured. Primary headaches frequencies were measured and were 32% for CTTH and 39% for CM. Chronic headaches showed a gender distribution of CTTH in males of 31%, in females 69%, CM in males was 15% and in females 85%. MOH in males was 25%, and in females 75%, which is similar to CTTH incidence. Frequency of CDH for MOH was 49.5% and CTTH was 32.7% and CM was 13.5%, which indicates that CTTH patients are different from CM patients in that CTTH patients are more likely to develop MOH as compared to CM patients. There was also a detectable and significant difference in the visual analog scale (VAS; validated, subjective measure for acute and chronic pain) score of 5.6 for CTTH versus 7 for CM; and 6.8 for CTTH/MOH versus 8 for CM/MOH. Age of onset of TTH was on average 30 years, whereas age of onset for migraine was 15 years. All these data point out that CTTH/MOH is a different disease as compared to CM/MOH because of distinctive pathophysiology, relapse rate, gender distribution (hormones), VAS score, age of onset and specific medication overused.

In respect of the treatment of MOH, Bendtsen et al. (J Headache Pain (2012) 13 (Suppl 1), pp. 1-29) recommend in their guidelines the discontinuation of all analgesics during a withdrawal period. However, abrupt discontinuation of overused analgesics often leads to withdrawal symptoms and rebound headache with migraine-like headaches and in some cases nausea, vomiting, sleep disturbances, agitation, anxiety, nervousness, hypotension and tachycardia. These symptoms have a duration of 2-10 days depending on the type of medication causing the overuse. Withdrawal symptoms may be treated during the first 1-2 weeks with levomepromazine, promethazine, metoclopramide and/or phenobarbital, and prophylactic treatment may be initiated after 2 months, i.e. when MOH had already been overcome.

The use of mirtazapine for treating TTH has been suggested for instance in EP1132082. Mirtazapine has also been suggested for the prophylaxis of TTH (Bendtsen et al., J Headache Pain (2012) 13 (Suppl 1), pp. 1-29). It has also been tried in a study to use low doses of mirtazapine in combination with ibuprofen for treating CTTH, however, it was found that such combination was not effective for the treatment of chronic tension type headache (Bendtsen et al., European Journal of Neurology 2007, 14, 187-193).

Therefore, it can be said that medication overuse headache based on tension-type headache has a different clinical picture, different pathophysiology, worse prognosis and higher relapse rate in comparison to medication overuse headache based on migraine. It is therefore an unmet need to treat and prevent medication overuse headache based on tension-type headache.

SUMMARY OF THE INVENTION

It is an object of the present invention to provide a medication and/or a treatment regimen for medication overuse headache based on tension-type headache and avoiding serious adverse effects due to medication overuse and withdrawal of overused medication. Thereby, it is to be noted that medication overuse headache is an own category of headache which is a secondary headache. In particular it is to be noted that medication overuse headache based on tension-type headache is distinct from medication overuse based on other headaches, such as for instance migraine.

The present application includes the following embodiments:
1. Mirtazapine for use in the treatment of medication overuse headache based on tension type headache.
2. Mirtazapine for the use according to embodiment 1, wherein the dosage is from 4 to 60 mg per day.
3. Mirtazapine for the use according to embodiment 1, wherein the dosage is from 10 to 48 mg per day.
4. Mirtazapine for the use according to any one of embodiments 1 to 3, wherein the treatment with mirtazapine is performed in parallel to the intake of overused medication(s).
5. Mirtazapine for the use according to any one of embodiment 4, wherein the parallel use of mirtazapine overlaps 1 to 24 weeks.
6. Mirtazapine for the use in the prophylaxis of relapsing medication overuse headache based on tension-type headache,
7. Mirtazapine for the use according to embodiment 6, wherein the prophylactic dosage is 4 to 40 mg of mirtazapine per day.
8. Mirtazapine for the use according to embodiment 6 or 7, wherein the prophylactic dosage is applied for 6 to 24 months.
9. Mirtazapine for the use according to any one of embodiments 1 to 8, wherein mirtazapine is administered once a day in the evening.
10. Mirtazapine for the use according to any one of embodiments 1 to 9, wherein medication overuse has developed from overuse of paracetamol, acetylsalicylic acid, non-steroidal anti-inflammatory drugs (NSAID), pyrazolones, opioids, or a combination of analgesics.
11. A pharmaceutical composition for the use in the treatment of medication overuse headache based on tension-type headache, comprising mirtazapine in an amount of 4 to 60 mg and a pharmaceutically acceptable excipient.
12. A pharmaceutical composition for the use in the prophylaxis relapsing medication overuse headache based on tension-type headache, comprising mirtazapine in an amount of 4 to 40 mg and a pharmaceutically acceptable excipient.
13. A pharmaceutical composition for the use according to embodiment 11 or 12, wherein the pharmaceutical composition is a tablet, an orodispersible tablet, a capsule, solution, a patch, a sublingual tablet, a nasal spray or an oral spray.

DETAILED DESCRIPTION OF THE INVENTION

Figure 1:
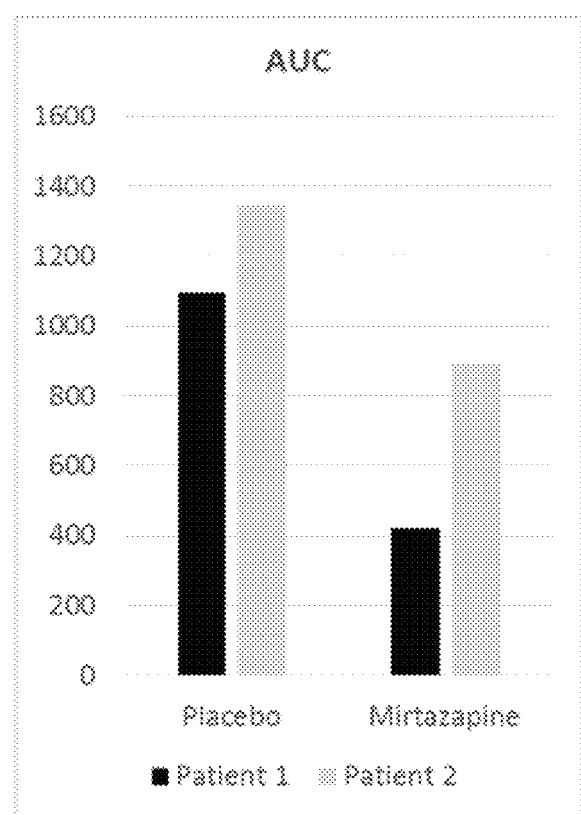
FIG. 1 shows the subject well-being of patients in a graph.

The present inventors have recognized that medication overuse headache based on tension-type headache can be treated specifically with mirtazapine. In particular, it is not necessary to first completely stop the treatment with acute painkillers as suggested in the literature. Reduction of overused analgesics may be performed gradually during treatment with mirtazapine. Thereby, acute headache pain and other withdrawal symptoms are ameliorated. However, medication overuse headache based on tension-type headache may also be treated with mirtazapine during overuse of analgesics. On the other hand, when medication overuse has been stopped, mirtazapine can help reduce tension-type headache, reduce withdrawal co-morbidities, increase the response rate of withdrawal, re-establish responsiveness to acute analgesic medication and prevent recurrence/relapse of tension-type headache.

(a) Medication overuse headache based on tension-type headache occurs in a patient with a pre-existing tension-type headache. The medication which is overused are analgetics.

(a1) Tension-type headache, which is a primary headache, is described as episodes of headache, with at least two of the following four characteristics:
1. Bilateral location
2. pressing or tightening (non-pulsating) quality
3. mild to moderate intensity
4. not aggravated by routine physical activity (such as walking or climbing stairs)
Both of the following:
1. no nausea or vomiting
2. no more than one of photophobia or phonophobia.

Tension-type headache can be divided into sub-groups such as infrequent episodic tension-type headache, frequent episodic tension-type headache and chronic tension-type headache.

(a2) Infrequent episodic tension-type headache has at least 10 episodes of headache occurring on <1 day per month on average (<12 days per year) with the symptoms given in (a1).

(a3) Frequent episodic tension-type headache has at least 10 episodes of headache occurring on 1-14 days per month on average for >3 months (≥12 and <180 days per year) and lasting from 30 minutes to 7 days, with the symptoms given in (a1).

(a4) Chronic tension-type headache means herein tension-type headache occurring ≥15 days per month for >3 months (≥180 days per year), and lasting hours to days, or unremitting, with the symptoms given in (a1).

In the present invention, MOH is associated with or based on tension-type headache, i.e. infrequent episodic tension-type headache, frequent episodic tension-type headache, and chronic tension-type headache; preferably frequent episodic tension-type headache, and chronic tension-type headache; more preferably chronic tension-type headache.

(b) In the present invention, the term "medication overuse headache (MOH) based on tension-type headache (TTH)" covers patients with a pre-existing primary tension-type headache who, in association with medication overuse, in particular analgesics overuse, develop a new type of headache or a marked worsening of their preexisting headache. Medication overuse headache is hence a secondary headache.

Medication overuse headache based on tension-type headache can be described as a headache occurring on 15 or more days per month developing as a consequence of regular overuse of acute or symptomatic headache medication for more than 3 months.

Diagnostic criteria for the definition of medication overuse headache based on tension-type headache, which is a secondary headache, are:

A. Tension-type headache occurring on ≥15 days per month in a patient with a pre-existing tension-type headache disorder;

B. Regular overuse for more than 3 months of one or more drugs that can be taken for acute and/or symptomatic treatment of headache.

Regular overuse for more than 3 months in this context means regular intake of acute and/or symptomatic headache medications for ≥10 days per month in case of overuse of opioids or combination-analgesic medications, and for ≥15 days per month in case of paracetamol (acetaminophen), acetylsalicylic acid, non-steroidal anti-inflammatory drug (NSAID) or pyrazolones.

The diagnosis of medication-overuse headache is extremely important clinically.

Approximately half of the people with headache on 15 or more days per month for more than 3 months have medication-overuse headache. Evidence shows that patients with this disorder may improve after discontinuation of the overused medication, as does their responsiveness to preventative treatment. However, such a detoxification is accompanied with withdrawal symptoms in addition to the severe headache which can in the initial phase of withdrawal even exacerbate. Such a detoxification is hard to bear and threatens the successful completion of the withdrawal therapy. The behavior of some patients with medication-overuse headache is similar to that seen with other drug addictions (Cephalalgia, 33(9) 629-808).

(c) Medication overuse headache based on tension-type headache means analgesics overuse of (Cephalalgia, 33(9) 629-808):
paracetamol (acetaminophen)
acetylsalicylic acid
non-steroidal anti-inflammatory drug (NSAID)
pyrazolones
opioids
combination-analgesics
medication-overuse headache attributed to multiple drug classes not individually overused Each of the above-mentioned overuses can individually or in combination with others lead to medication overuse headache.

Specifically, paracetamol (acetaminophen)-overuse headache means regular intake of paracetamol (acetaminophen) on ≥15 days per month for >3 months.

Specifically, acetylsalicylic acid-overuse headache means regular intake of acetylsalicylic acid on ≥15 days per month for >3 months.

Specifically, non-steroidal anti-inflammatory drug (NSAID)-overuse headache means regular intake of non-steroidal anti-inflammatory drug (NSAID) on ≥15 days per month for >3 months.

Specifically, opioid-overuse headache means regular intake of opioids on ≥10 days per month for >3 months.

Specifically, combination-analgesic-overuse headache means regular intake of combination-analgesic medications on ≥10 days per month for >3 months. Thereby, the term combination-analgesic is used for formulations combining drugs of two or more classes, each with analgesic effect or acting as adjuvants.

Specifically, medication-overuse headache attributed to overuse of multiple drug classes means regular intake of any one of paracetamol, acetylsalicylic acid, NSAIDs, pyrazolones, and/or opioids.

(d) In the present invention, the term "mirtazapine" relates to the racemate (RS)-(±)-2-methyl-1,2,3,4,10,14b-hexahydropyrazino[2,1-a]pyrido[2,3-c][2]benzazepine of the formula $C_{17}H_{19}N_3$ as well as to each single S- or R-enantiomer and to mixtures thereof in any ratio. The molecular weight is 265.35 g/mol. The CAS number is 61337-67-5 and 85650-52-8 for (RS)-Mirtazapine. Its structure is as follows:

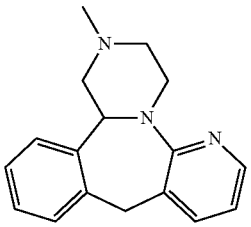 [SMILES: CN1CCN2c3ncccc3Cc3ccccc3C2C1]

Mirtazapine comprises the (R)-enantiomer and the (S)-enantiomer.

Mirtazapine is a tetracyclic antidepressant with noradrenergic and specific serotonergic effects (Kent et al., Lancet 2000, 355, 911-918). Mirtazapine blocks alpha-adrenergic receptors on noradrenergic and serotonergic presynaptic neurons, which results in increased serotonergic and noradrenergic neurotransmission (Westenberg et al., J. Clin. Psychiatry 1999; 60 (suppl. 17), 4-8).

Its use in the prophylactic treatment of chronic tension-type headache cTTH has been reported (Bendtsen et al., Neurology 62, 2004, 1706-1711). However, its usability and efficacy in the treatment of medication overuse headache based on tension-type headache has not been subject to research.

(1) Hence, a first embodiment relates to mirtazapine for use in the treatment of medication overuse headache (MOH) based on tension-type headache (TTH). Thereby, the MOH still exists when the treatment with mirtazapine is started. The withdrawal of overused medicaments before the start of the treatment with mirtazapine is not required. In other words, such embodiment relates to mirtazapine for use in the treatment of existent MOH based on TTH. MOH is not pre-treated by withdrawal of overused medication. MOH is diagnosed, symptomatic and clinically present.

Medication overuse headache based on tension-type headache is thereby defined as stated in (b) above, in particular as follows
  A. Tension-type headache occurring on ≥15 days per month in a patient with a pre-existing primary tension-type headache disorder;
  B. Regular overuse for more than 3 months of one or more drugs that can be taken for acute and/or symptomatic treatment of headache.

Regular overuse for more than 3 months in this context means regular intake of acute and/or symptomatic headache medicaments for ≥10 days per month in case of overuse of opioids or combination-analgesic medications, and/or for ≥15 days per month in case of paracetamol (acetaminophen), acetylsalicylic acid, non-steroidal anti-inflammatory drug (NSAID) or pyrazolones.

In the present invention, MOH is associated with or based on infrequent episodic tension-type headache, frequent episodic tension-type headache, and chronic tension-type headache; preferably frequent episodic tension-type headache, and chronic tension-type headache; more preferably chronic tension-type headache.

(2) A further embodiment relates to mirtazapine for use in the treatment of medication overuse headache based on tension-type headache, wherein the dosage is from 4 to 60 mg per day. Preferably, the lower range starts from 4, 5, 6, 7, 8, 9, 10, 11, 12, 13, 14 or 15 mg per day. Preferably the higher range ends with 60 to 36 mg per day, i.e. 36, 40, 42, 45, 48, 50, 55, 60 mg per day. It is to be understood that every starting point of the lower range can be combined with every end point of the higher range. Preferred ranges are for example 4 to 60 mg per day, 6 to 60 mg per day, 6 to 55 mg per day, 6 to 48 mg per day, 6 to 36 mg per day, 10 to 60 mg per day, 10 to 55 mg per day, 10 to 48 mg per day, 10 to 45 mg per day, 10 to 36 mg per day, 12 to 60 mg per day, 12 to 55 mg per day, 12 to 50 mg per day, in particular 12 to 48 mg per day, 12 to 36 mg per day, 12 to 24 mg per day. Particularly preferred doses are 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg or 60 mg per day. Also preferred are 6 to 48 mg, e.g. 6 mg, 12 mg, 18 mg, 24 mg, 36 mg, 48 mg per day. Further preferred are 10 mg, 20 mg, 30 mg and 40 mg. Further preferred are 10 mg, 20 mg and 40 mg.

(3) A further embodiment relates to mirtazapine for use in the treatment of medication overuse headache based on tension-type headache according to any one of the preceding embodiments, wherein the treatment with mirtazapine is performed in parallel to the intake of overused medication (s). This means that mirtazapine is already administered during abuse of other medication, in particular analgesics. Thereby, the symptoms of medication overuse headache are ameliorated. This means that headache duration as well as headache intensity decrease, even though the former medications/analgesics are further abused. However, it is also possible that the amount of overused medication is lowered during the intake of mirtazapine, and may be even discontinued.

(4) A further embodiment relates to mirtazapine for use in the treatment of medication overuse headache based on tension-type headache according to any one of the preceding embodiments, wherein the treatment dose is started as long as the overused medicament is still used, i.e. use or overuse of the medicament and treatment dose with mirtazapine is overlapping. Thereby, the overlap or parallel treatment is at least for a certain time. Preferable, the time of overlap or parallel use is 1 to 24 weeks, 1 to 20 weeks, 1 to 18 weeks, 3 to 20 weeks, 3 to 18 weeks, 4 to 18 weeks or 5 to 18 weeks.

(5) A further embodiment relates to mirtazapine for use in the prophylaxis of medication overuse headache based on tension-type headache, preferably relapsing medication overuse headache based on tension-type headache.

Thereby, mirtazapine is used for the prophylaxis of relapsing medication overuse headache based on tension-type headache in a prophylactic dosage. In particular, mirtazapine is used for the prophylaxis of medication overuse headache based on tension-type headache. Thereby, the prophylactic mirtazapine dosage is preferably 4 to 40 mg per day, for instance 6 to 40 mg, 6 to 35 mg, 6 to 30 mg, 6 to 24 mg, 6 to 20 mg, 6 to 18 mg, 10 to 30 mg, 10 to 25 mg, 10 to 24 mg, 12 to 24 mg per day. The daily prophylactic dosage of mirtazapine may for instance be 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 mg per day. It is to be understood that each of the given daily dosages can be regarded as a lower or an upper range.

(6) In a further embodiment according to embodiment (5) it can be desired that the prophylactic dosage of mirtazapine against relapsing medication overuse headache based on tension-type headache is applied or continued for a certain time. The prophylactic dosage is as disclosed in embodiment (5). In such a situation, the prophylactic dosage is preferably applied for 6 to 24 months in order to prevent occurrence or worsening of primary headache and medication overuse headache. For instance, the prophylactic treatment is applied for 6 to 18 months, for instance 12 months.

(7) In a further embodiment according to any one of the preceding embodiments, the present invention relates to mirtazapine for the use in the treatment of medication overuse headache based on tension-type headache or in the prophylaxis of relapsing medication overuse headache based on tension-type headache, wherein the dosage according to embodiment (2) or (5) is administered once a day in the evening, preferably before bedtime.

Mirtazapine can be taken independently from meals. However, administration once a day, namely in the evening, preferably before bedtime, is recommended.

(8) In a further embodiment according to any one of the preceding embodiments, the medication overuse has developed from an overuse of paracetamol, acetylsalicylic acid, non-steroidal anti-inflammatory drugs (NSAID), pyrazolones, opioids, or a combination of analgesics.

Examples for non-steroidal anti-inflammatory drugs are diclofenac, dexibuprofen, diflunisal, etodolac, fenoprofen, flufenamic acid, fluroprofen, ibuprofen, ondomethacin, ketoprofen, ketorolac, lornoxicam, meclofenamic acid, mefenamic acid, meloxicam, nabumetone, naproxen, oxaprocin, piroxicam, salsalate, sulinac tenoxicam, tolmetin, tofenamic acid. Examples for pyrazolones are metamizole (e.g. as metamizole sodium salt, metamizole sodium monohydrate), propyphenazone, phenazone, aminophenazone, and phenylbutazone, preferred are metamizole and propyphenazone. Examples for opioids are alfentanil, benzhydrocodone, buprenorphine, codeine, dermorphin, desomorphin, dextromoramide, dihydrocodeine, ethylmorphin, fentanyl, heroin, hydromorphone, levomethadone, methadone, morphine, nalbuphine, opium, oxycodone, oxymorphone, pethidine, piritramide, remifentanil, sufentanil, tapentadol, tilidine, or tramadol.

(9) A further embodiment relates to a pharmaceutical composition for the use in the treatment of medication overuse headache based on tension-type headache, comprising mirtazapine in an amount of 4 to 60 mg and at least one pharmaceutically acceptable excipient. Preferably, the amount of mirtazapine is as described in embodiment (2) above.

(10) A further embodiment relates to a pharmaceutical composition for the use in the prophylaxis of relapsing medication overuse headache based on tension-type headache, comprising mirtazapine in an amount of 4 to 40 mg and at least one pharmaceutically acceptable excipient. Preferably, the amount of mirtazapine is as described in embodiment (5) above.

A pharmaceutically acceptable excipient is for instance crospovidone (type B), mannitol (E421), cellulose, microcrystalline (E460), aspartame (E951), silica, colloidal anhydrous, magnesium stearate (E572), strawberry guarana flavor [maltodextrin, propylene glycol, artificial flavors, acetic acid (<1%)], and peppermint flavor [artificial flavors, corn starch].

(11) In a further embodiment, the invention relates to a pharmaceutical composition according to embodiment (9) or (10), wherein the pharmaceutical composition is a tablet, an orodispersible tablet, a capsule, solution, patch, a sublingual tablet, a nasal spray or an oral spray. In one sub-embodiment, such formulations are prepared for sustainable release of active ingredient mirtazapine.

(12) In a further embodiment, the invention relates to the use of mirtazapine for the manufacture of a medicament for the treatment of medication overuse headache based on tension-type headache.

Mirtazapine may be comprised in an amount as described in embodiment (2), and the medicament may be used for the treatment regimen as described in embodiments (3), (4), (6) and (7), as well as for the purpose of embodiment (8) above. It is to be understood, that each of the disclosed embodiments may be regarded as disclosed also in the form of the use of mirtazapine for the manufacture of a medicament for the treatment of medication overuse based on tension-type headache.

Examples of such further embodiments are (12.1) The use of mirtazapine for the manufacture of a medicament for the treatment of medication overuse headache based on tension-type headache according to (12), wherein the dosage is 4 to 60 mg mirtazapine per day. The disclosure of embodiment (2) applies accordingly.

(12.2) The use according to (12) or (12.1), wherein the dosage is 10 to 48 mg mirtazapine per day. The disclosure of embodiment (2) applies accordingly.

(12.3) The use according to any one of (12) to (12.2), wherein the treatment with mirtazapine is performed in parallel to the intake of overused medication(s). The disclosure of embodiment (3) applies accordingly.

(12.4) The use according to any one of (12) to (12.3), wherein the parallel use of mirtazapine overlaps for 1 to 24 weeks. The disclosure of embodiment (4) applies accordingly.

(12.5) The use according to any one of (12) to (12.4), wherein mirtazapine is used for the prophylaxis of medication overuse headache based on tension-type headache, preferably for the prophylaxis of relapsing medication overuse headache based on tension-type headache. Preferably, the prophylactic dosage is 4 to 40 mg per day. The disclosure of embodiment (5) applies accordingly.

(12.6) The use according to (12.5), wherein the prophylactic dosage is applied for 6 to 24 months. The disclosure of embodiment (6) applies accordingly.

(12.7) The use according to any one of (12) to (12.6), wherein the mirtazapine is administered once per day, in the evening. The amount of mirtazapine may be as described in embodiments (2) and (5). The disclosure of embodiment (7) applies accordingly.

(12.8) The use according to any one of (12) to (12.7), wherein medication overuse has developed from overuse of paracetamol, acetylsalicylic acid, non-steroidal anti-inflammatory drugs (NSAID), pyrazolones, opioids, or a combination of analgesics. The disclosure of embodiment (8) applies accordingly.

(13) In a further embodiment, the invention relates to a method for treatment of medication overuse headache based on tension-type headache, comprising administering to a patient in need thereof a therapeutically efficient amount of mirtazapine.

Mirtazapine may be applied in an amount as described in embodiment (2), and for the purposes as described in embodiments (3), (4) and (6) to (8) above.

It is to be understood, that each of the disclosed embodiments may be regarded as disclosed also in the form of a method for treating medication overuse headache in a human in need of such treatment.

Examples of such further embodiments are (13.1) The method according to (13), comprising administering to a patient in need thereof 4 to 60 mg mirtazapine per day. The disclosure of embodiment (2) applies accordingly.

(13.2) The method according to (13), comprising administering to a patient in need thereof 10 to 48 mg mirtazapine per day. The disclosure of embodiment (2) applies accordingly.

(13.3) The method according to any one of (13) to (13.2), comprising administering mirtazapine in parallel to the intake of overused medicament(s). The disclosure of embodiment (3) applies accordingly.

(13.4) The method according to any one of (13) to (13.3), comprising administering mirtazapine in parallel to the intake of overused medicament(s) for 1 to 24 weeks. The disclosure of embodiment (4) applies accordingly.

(13.5) The method according to any one of (13) to (13.4), wherein the mirtazapine is used for the prophylaxis of medication overuse headache based on tension-type headache, in particular of relapsing medication overuse headache based on tension-type headache. Thereby, mirtazapine is preferably in a dose of 4 to 40 mg per day. The disclosure of embodiment (5) applies accordingly.

(13.6) The method according to (13.5), comprising administering to a patient in need thereof the prophylactic dosage for 6 to 24 months. The disclosure of embodiment (6) applies accordingly.

(13.7) The method according to any one of (13) to (13.6), comprising administering to a patient in need thereof a therapeutically or prophylactically efficient amount of mirtazapine once per day, in the evening. The amount of mirtazapine may be as described in embodiments (2) and (5). The disclosure of embodiment (7) applies accordingly.

(13.8) The method according to any one of (13) to (13.7), wherein medication overuse has developed from overuse of paracetamol, acetylsalicylic acid, non-steroidal anti-inflammatory drugs (NSAID), pyrazolones, opioids or a combination of analgesics. The disclosure of embodiment (8) applies accordingly.

ABBREVIATIONS cTTH chronic tension-type headache
feTTH frequent episodic tension-type headache
ieTTH infrequent episodic tension-type headache
MOH medication overuse headache
NSAID non-steroidal anti-inflammatory drug
TTH tension-type headache

EXAMPLE a) Patients had daily medication overuse headache (MOH) originating from daily analgesic use primarily against tension-type headache as primary headache. They were treated first with placebo for 8 weeks, followed by two weeks of wash-out (taking placebo), and then administration of 15 to 30 mg of mirtazapine per day for 8 weeks. During that time they were allowed to continue taking their analgesics as usual, if they felt it was necessary.

At the same time, they had to keep a diary where they had to write down the frequency and duration of their headache as well as the headache intensity. After completion of the study the diaries were evaluated and the daily recordings of headache duration was multiplied with headache intensity to give the "AUC", which means "area under the curve". The results shown in table 1 and table 2 below are from the last four weeks of intake of either placebo or mirtazapine. Patient 1 showed a strong placebo effect, whereas patient 2 did not. It can be seen that both patients experienced improvement of their headache upon administration of mirtazapine.

TABLE 1

| | AUC | | |
|---|---|---|---|
| | Placebo | Mirtazapine | Reduction |
| Patient 1 | 1097 | 420 | 62% |
| Patient 2 | 1348 | 895 | 34% | b) Moreover, the intake of overused analgesic medication was recorded by the same patients and during the time frame as described above in (a). Patient 1 reduced the intake of overused medication by 80% (Table 2). As for patient 2, the reduction is 15%, whereby both patients additionally benefit from improved well-being, i.e. from decreased number of headache attacks, shorter headache attacks with lower headache intensity (see above).

Therefore, these data suggest that continuous treatment with mirtazapine during and after analgesics overuse prevents new medication overuse, and also is able to improve the well-being of patients by an overall reduction in headache attacks.

TABLE 2

| | Analgesics Usage | | |
|---|---|---|---|
| | Placebo | Mirtazapine | Reduction |
| Patient 1 | 10 | 2 | 80% |
| Patient 2 | 55 | 47 | 15% |

DESCRIPTION OF THE FIGURES

FIG. 1 depicts the subjective well-being of patients, i.e. decreased number of headache attacks, shorter headache attacks with lower headache intensity. The lower the count of the y-axis, the better is the subjective well-being. AUC means area under the curve. AUC was calculated as the sum of the daily recordings of headache duration multiplied with headache intensity.

Figure 2:
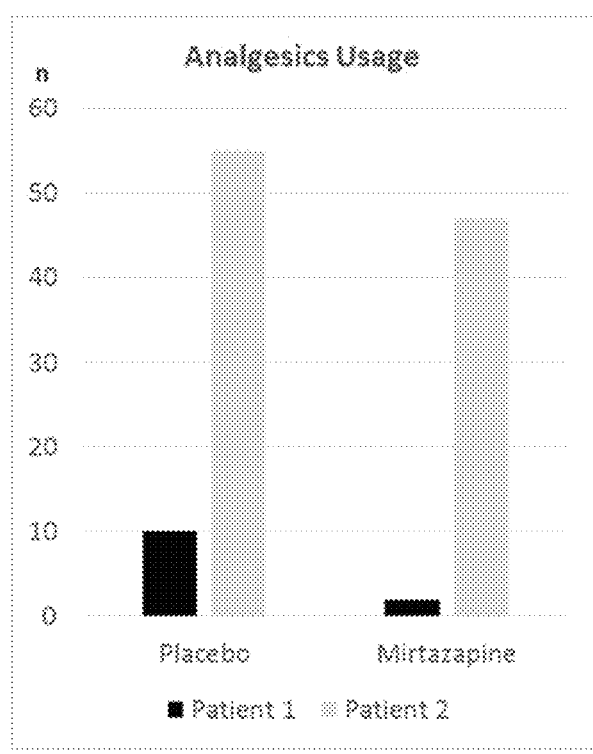
FIG. 2 shows the intake of analgesics of the same patients in a graph.

FIG. 2 shows n=the intake of overused analgesic medication of the same patients during the placebo and mirtazapine treatment.

Numerous modifications and variations on the present invention are possible in light of the above teachings. It is therefore to be understood that within the scope of the appended embodiments, the invention may be practiced otherwise than as specifically described herein.

The invention claimed is:

1. A method for treatment of medication overuse headache based on tension-type headache, the method comprising: administering to a patient in need thereof a therapeutically efficient amount of mirtazapine in parallel to the intake of one or more overused medicament,
    wherein the medication overuse headache is a secondary headache where the patient has a pre-existing primary tension-type headache and, in association with medication overuse, develops a new type of headache or a marked worsening of the pre-existing tension-type headache, and
    wherein the medication overuse headache develops from overuse of paracetamol, acetylsalicylic acid, non-steroidal anti-inflammatory drugs (NSAID), pyrazolones, opioids, or a combination of analgesics.

2. The method according to claim 1, wherein the amount of mirtazapine is 4 to 50 mg mirtazapine per day.

3. The method according to claim 1, wherein the amount of mirtazapine is 10 to 48 mg mirtazapine per day.

4. The method according to claim 1, wherein the parallel intake of the one or more overused medicaments is 1 to 24 weeks.

5. The method according to claim 1, wherein the mirtazapine reduces the likelihood of occurrence for relapsing medication overuse headache based on a tension-type headache.

6. The method according to claim 5, wherein the amount of mirtazapine is 4 to 40 mg.

7. The method according to claim 5, wherein a dosage of mirtazapine is administered for 6 to 24 months.

8. The method according to claim 1, wherein mirtazapine is administered once per day, in the evening.

9. The method according to claim 5, wherein mirtazapine is administered once per day, in the evening.

10. The method according to claim 1, wherein the mirtazapine is administered after treatment of the pre-existing primary tension-type headache.

11. The method according to claim 1, wherein the mirtazapine is administered during withdrawal from the overused medication.

12. The method according to claim 1, wherein the medication overuse is regular overuse of acute or symptomatic headache medication for more than three months.

* * * * *

UNITED STATES PATENT AND TRADEMARK OFFICE
CERTIFICATE OF CORRECTION

PATENT NO. : 11,207,330 B2  
APPLICATION NO. : 16/948813  
DATED : December 28, 2021  
INVENTOR(S) : Arnim Pause et al.

Page 1 of 1

It is certified that error appears in the above-identified patent and that said Letters Patent is hereby corrected as shown below:

In the Specification

Column 7, Lines 32-33, "(5)-enantiomer." should read --(S)-enantiomer.--;

Column 7, Lines 60, "215 days" should read --≥15 days--.

Signed and Sealed this  
Fifteenth Day of March, 2022

Drew Hirshfeld  
*Performing the Functions and Duties of the*  
*Under Secretary of Commerce for Intellectual Property and*  
*Director of the United States Patent and Trademark Office*